United States Patent
Willis

(10) Patent No.: US 9,032,556 B2
(45) Date of Patent: May 19, 2015

(54) PHYSICAL TREATMENT GARMENT

(71) Applicant: JDUBBS, LLC, Naperville, IL (US)

(72) Inventor: Gerald C. Willis, Naperville, IL (US)

(73) Assignee: JDUBBS, LLC., Naperville, IL (US)

( * ) Notice: Subject to any disclaimer, the term of this patent is extended or adjusted under 35 U.S.C. 154(b) by 0 days.

(21) Appl. No.: 14/222,611

(22) Filed: Mar. 22, 2014

(65) Prior Publication Data

US 2014/0283281 A1 Sep. 25, 2014

Related U.S. Application Data

(60) Provisional application No. 61/804,594, filed on Mar. 22, 2013.

(51) Int. Cl.
*A41D 1/08* (2006.01)
*A41D 1/06* (2006.01)

(52) U.S. Cl.
CPC ........................................ *A41D 1/06* (2013.01)

(58) Field of Classification Search
USPC ............. 2/228, 238, 79, 227, 242; 128/100.1, 128/101.1, 96.1
See application file for complete search history.

(56) References Cited

U.S. PATENT DOCUMENTS

| | | | | | |
|---|---|---|---|---|---|
| 4,325,379 | A | * | 4/1982 | Ozbey | 450/116 |
| 5,536,246 | A | * | 7/1996 | Saunders | 602/19 |
| 5,857,947 | A | * | 1/1999 | Dicker et al. | 482/124 |
| 6,231,488 | B1 | * | 5/2001 | Dicker et al. | 482/124 |
| 7,246,381 | B2 | * | 7/2007 | Green | 2/69 |
| 8,214,926 | B2 | * | 7/2012 | Brown | 2/228 |
| 8,597,222 | B2 | | 12/2013 | Lucero | |

* cited by examiner

*Primary Examiner* — Tejash Patel
(74) *Attorney, Agent, or Firm* — Chicago IP Law; Steven M. Evans

(57) ABSTRACT

Physical treatment garment for aiding in treatment and healing of injured or strained muscles. Garment is made of flexible material that can be pulled up around the waist, such as compression shorts or full length tights or leggings, and the garment has one or more pockets in the thigh and/or hamstring area to hold cold packs or heat packs and have a fastener apparatus at the top. The garment has fastening apparatuses on or about the hip area and on or about just above the knee. Using a flexible or compression wrap with the compatible fastening apparatuses, the compression wrap is wrapped around the leg and/or groin area and secured using the fastening apparatuses. Pockets for ice or heat treatment are similarly located in the front or rear of the tights or leggings with fastening connections to hold ice or heat packs for treatment of the applicable injury.

18 Claims, 10 Drawing Sheets

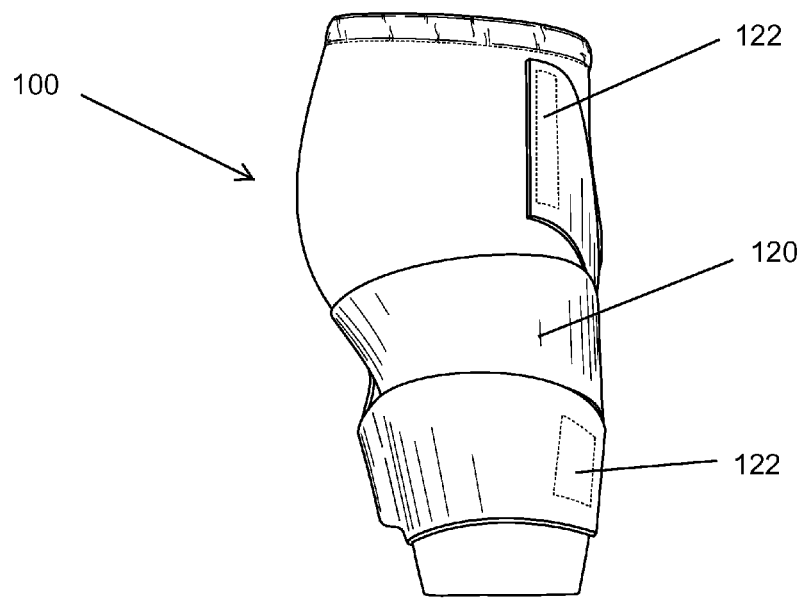
FIG. 9
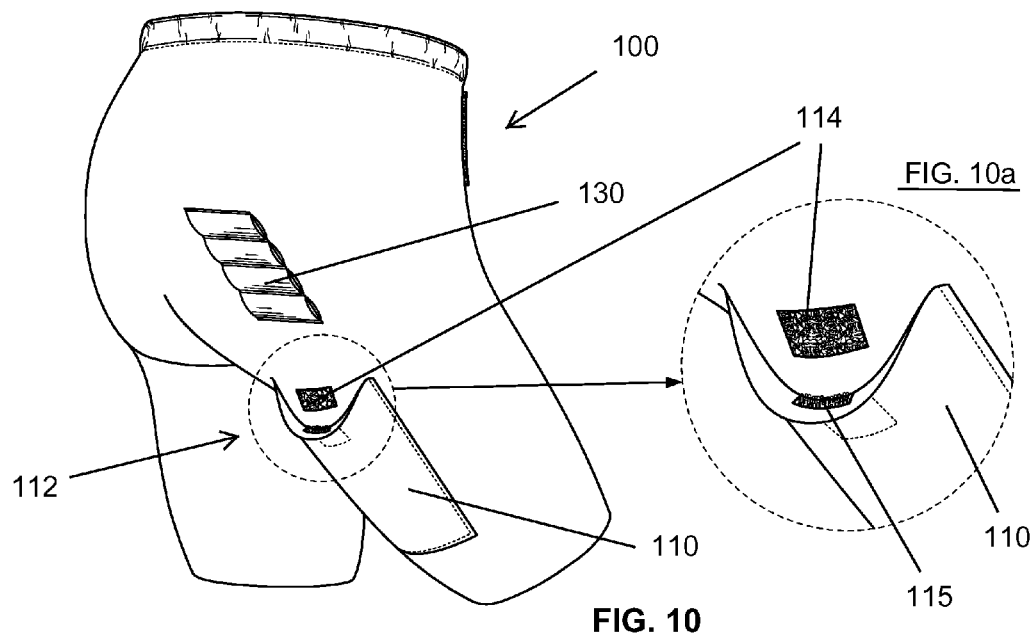
FIG. 10a
FIG. 10

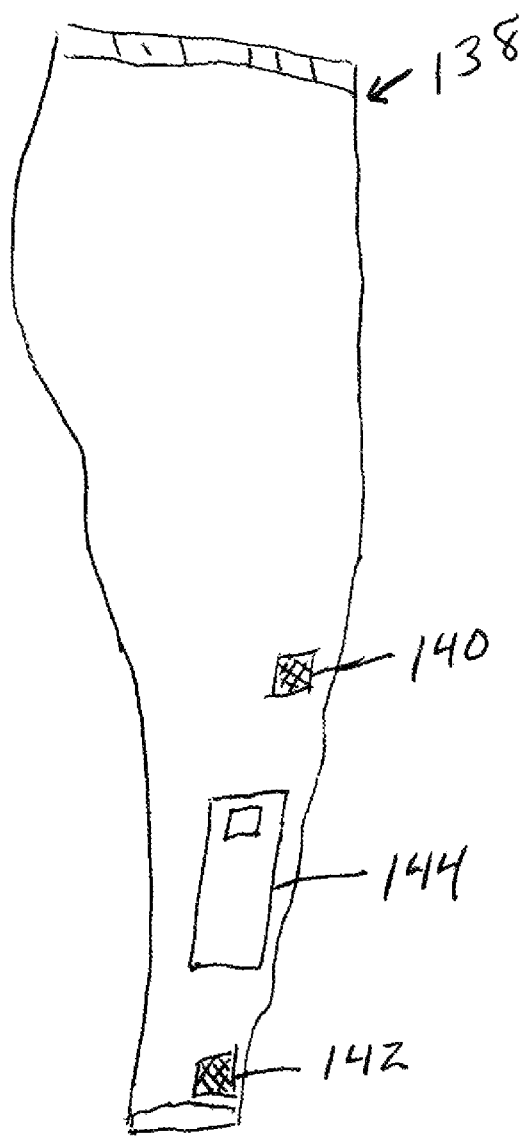

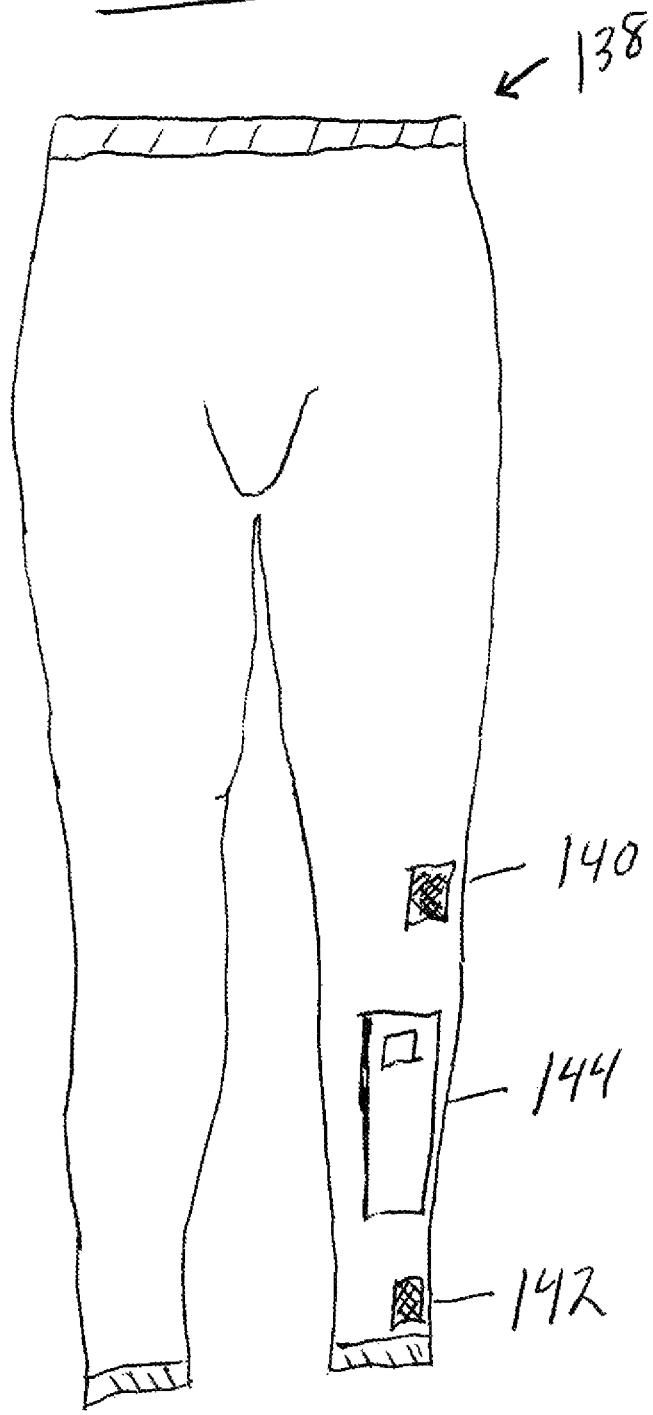

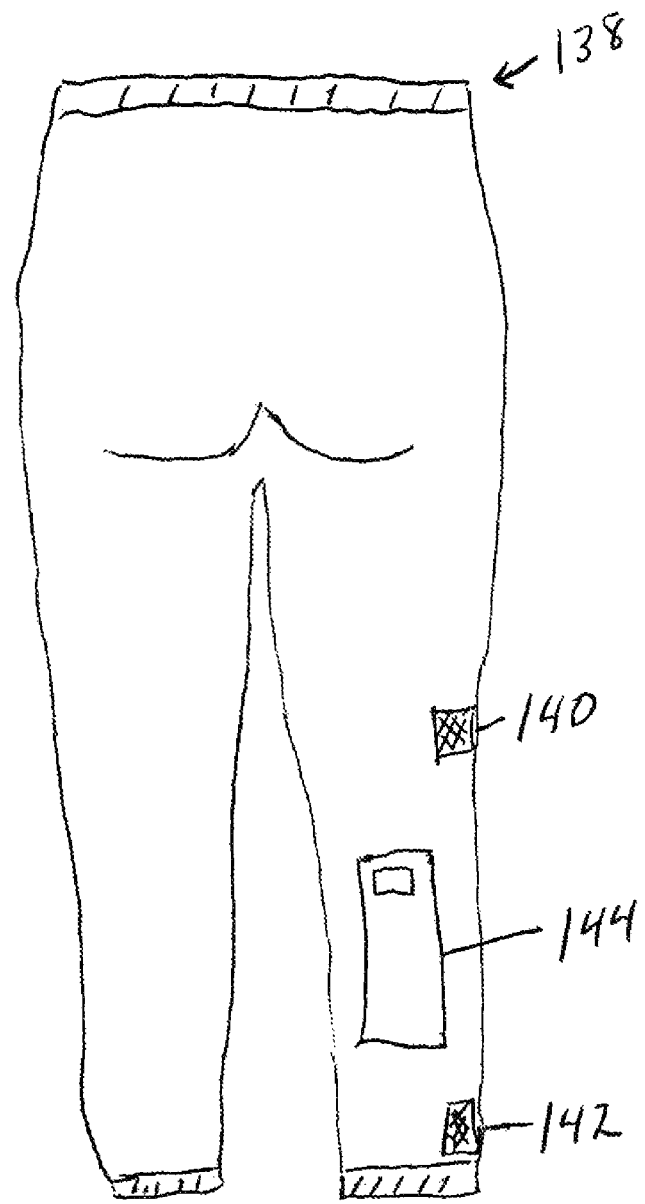

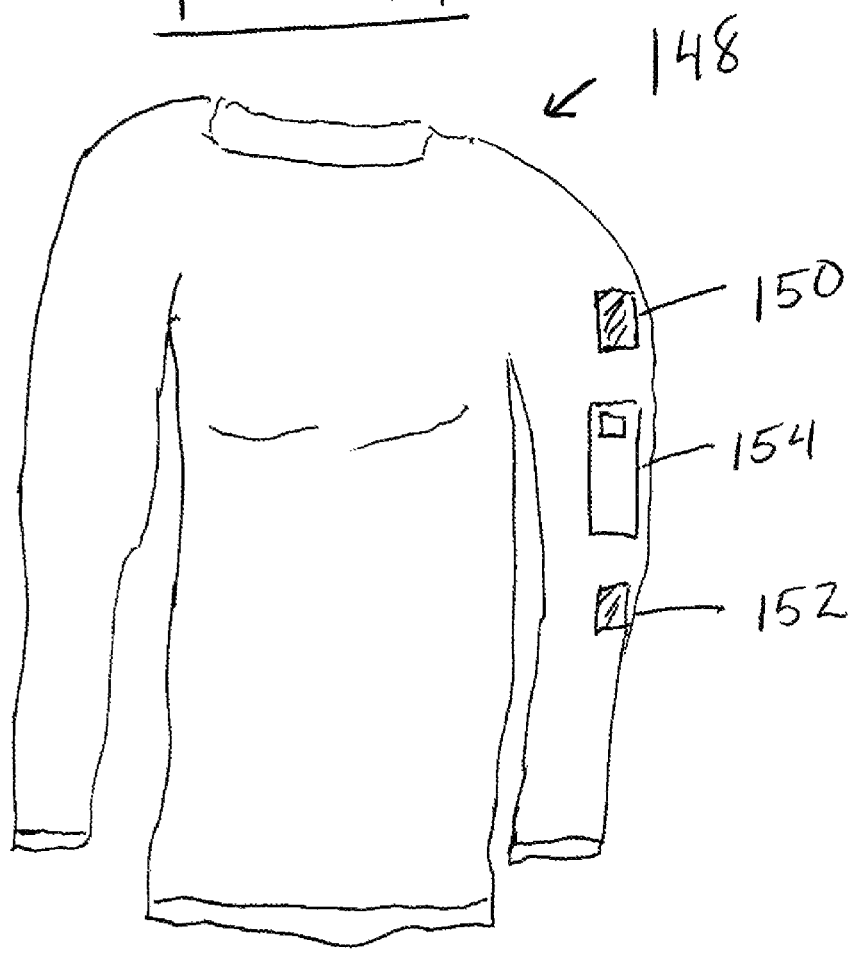

PHYSICAL TREATMENT GARMENT

CROSS-REFERENCE TO RELATED APPLICATION

This non-provisional patent application claims priority and benefit of U.S. provisional patent application having application No. 61/804,594, filed on Mar. 22, 2013, and entitled "Medical Treatment Garment," which is hereby incorporated by reference.

BACKGROUND OF THE INVENTION

1. Field of the Invention

The present invention relates generally to support garments for treating muscle injuries.

2. Description of Related Art

Compression wraps used to treat muscle and other soft tissue injuries and discomforts typically involve wrapping a compression wrap around a person's body and securing the ends of the compression wrap to the body with hook and loop material, metal clips, or tape to hold the wrap in place. There are also flexible sleeves that can be pulled up from the foot to the thigh to create compression of the muscle, which is typically one of the treatments for an injured muscle. However, a constant problem typically experienced with these devices, particularly when used to treat a lower body injury, is that the devices tend to slide out of place, such as sliding down the leg when walking or otherwise moving about. Another problem when recovering from an injury using typical flexible wraps is icing or heating the injured area. In particular, if a user needs to walk or move about, the ice or heat device typically falls out of the wrap or slides out of place. If an athlete has a strained muscle, the athlete is often able to participate in athletic events if wrapped or taped. However, humidity, perspiration and constant movement often lead to a wrap coming undone.

Accordingly, there is a need for an improved design for compression wraps that remain secured in place and at the desired location on a user's body during activity, as well as the ability to apply ice and heat treatment while still being able to move about during regular daily activity.

ASPECTS AND SUMMARY OF THE PRESENT INVENTION

One aspect of the present invention is to provide compression wraps that remained secured to a user's body and do not come undone.

Another aspect of the present invention is to provide compression wraps that remain in desired locations on a user's body and do not slip or slide to another location during activity of a user.

A further aspect of the present invention is to provide improved clothing that secures compression wraps in a desired location and allows for the treatment by ice and/or cold packs and/or heat packs in a secured pocket to treat the injured area.

An additional aspect of the present invention is to improve the comfort and recovery time of persons who suffer a muscle or ligament injury and to be able to treat the injury more effectively.

Another aspect of the present invention is to support minor strains while further allowing an individual to participate uninterrupted in daily activities.

In order to achieve these aspects, the present invention provides a physical treatment garment having a pair of flexible shorts constructed of flexible material, a plurality of fastening apparatuses on multiple fastening areas on the pair of shorts, and a flexible wrap having a first end with a fastening apparatus and a second end with a fastening apparatus for releasably coupling the flexible wrap to the fastening apparatuses on the shorts, wherein the first end and the second end of the flexible wrap each can be attached a fastening apparatus on the flexible shorts to apply compression to an injured area, and the flexible wrap can be completely removed from the shorts for washing and cleaning. The plurality of the fastening apparatuses on the flexible shorts preferably are located on an upper portion proximate to a hip and waist area of the flexible shorts, and a plurality of the fastening apparatuses that are preferably located on the flexible shorts at a lower portion of the flexible shorts that are proximate just above a knee area, wherein the flexible wrap can be connected to the flexible shorts between the upper portion and the lower portion of the flexible shorts to provide compression treatment to thigh, groin and hamstring areas of a user's body.

The foregoing, as outlined rather broadly, the preferred features of the present invention so that those skilled in the art may better understand the detailed description of the invention that follows. Additional features of the invention will be described hereinafter that form the subject of the claims of the invention. Those skilled in the art should appreciate that they can readily use the disclosed invention and specific embodiments as a basis for designing or modifying other structures for carrying out the same purposes of the present invention, and that such other structures do not depart from the spirit and scope of the invention in its broadest form.

BRIEF DESCRIPTION OF THE DRAWINGS

FIG. 9 is a side perspective view of the compression shorts shown in FIG. 5D, wherein a compression wrap is secured to the right leg;

FIG. 10 is a rear perspective view of the compression shorts shown in FIGS. 1-4, wherein a pocket on the rear of the right let is illustrated having a sealing apparatus for holding a hot or cold pack within the pocket;

FIG. 10a is an enlarged perspective view of the fastening apparatus shown in FIG. 10;

FIG. 11 is a side view of a full length physical therapy garment pants configured in accordance with another embodiment of the present invention;

FIG. 12 is a front view of the full length physical therapy garment shown in FIG. 11;

FIG. 13 is a rear view of the physical therapy garment shown in FIGS. 11 and 12; and FIG. 14 is a front perspective view of a full length physical therapy garment shirt configured in accordance with another embodiment of the present invention.

DETAILED DESCRIPTION OF THE PREFERRED EMBODIMENTS

Figure 1:
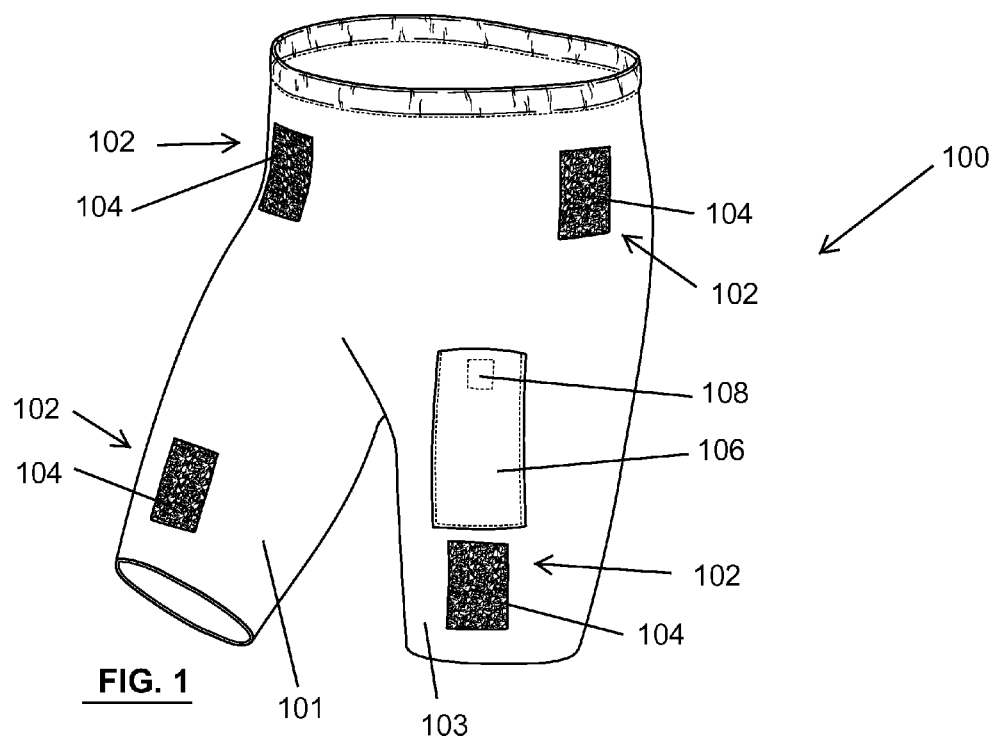
FIG. 1 is a front perspective view of compression shorts configured in accordance with a preferred embodiment of the present invention.

Referring now to the drawings, FIG. 1 shows a front view of a physical treatment garment 100 configured in accordance with a preferred embodiment of the present invention. The physical treatment garment preferably is compression shorts 100. Compression shorts 100 are generally constructed of tight flexible fabric, such as polyester, elastane, or spandex.

In accordance with the present invention, a pair of shorts, leggings or flexible or compression shorts 100 are provided that are form fitting from the waist to just above the knee, and fastening areas 102 are located at the hip and waist area on the shorts 100. The fastening areas 102 include fastening apparatuses 104, such as a patch of loops-and-hooks. One type of patch of loops-and-hooks is Velcro®. Other types of fastening, connecting, or securing apparatuses 104 include snaps, zippers or buttons, but loops-and-hooks such as Velcro® are preferred. The purpose of the loops-and-hooks in this area is to secure a compression wrap to the fastening areas 102, wherein the loops-and-hooks or other type of fastening apparatus 104 secures a flexible wrap to the shorts in a desired location and prevents the compression wrap from sliding down the leg of the compression shorts 100.

Figure 2:
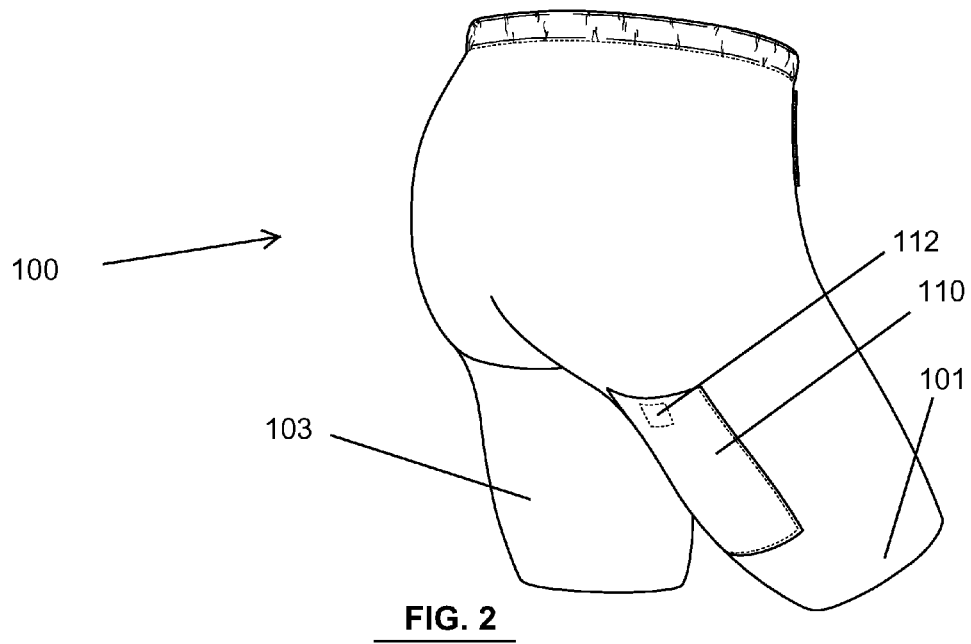
FIG. 2 is a rear perspective view of the compression shorts shown in FIG. 2.

FIGS. 1 and 2 also illustrate a pocket 106 on the left front leg 103 of the compression shorts 100, and a pocket 110 on the back of the right leg 101 of the flexible or compression shorts 100. A closing apparatus 108 is used to close the pocket 106 on the left leg 103, and a closing apparatus 112 is used to close the pocket 110 on the right leg. The pockets 106, 110 preferably are constructed of the same material and thickness as the compression shorts 100, and preferably secured to the shorts 100 by stitching and/or glue. The closing apparatuses 108, 112 are preferably loops-and-hooks, such as Velcro®, attached to the inside wall of the top of the pockets 106, 110 and a directly opposing location on the outside of the shorts 100. In other embodiments the closing apparatuses can be buttons and button holes, zippers, or snaps.

Figure 3:
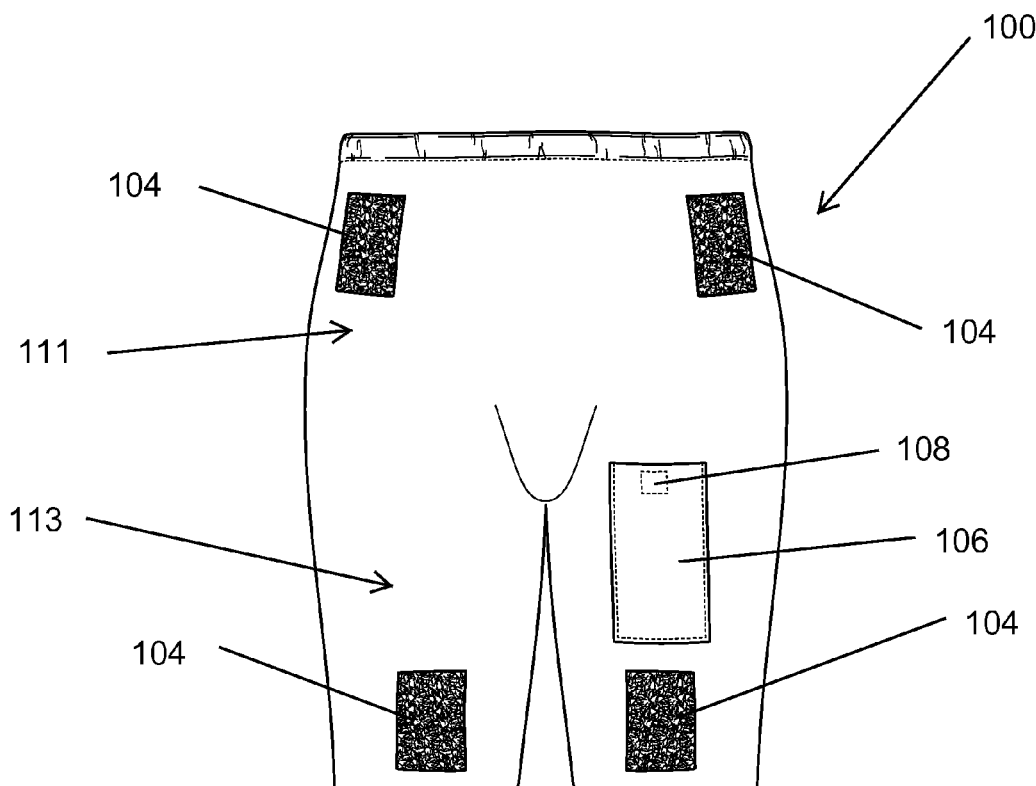
FIG. 3 is a front view of the compression shorts shown in FIGS. 1 and 2.

FIG. 3 is a front perspective view of the compression shorts 100 shown in FIGS. 1 and 2. FIG. 3 illustrates the fastening apparatuses on the upper portion 111 of the compression shorts 100, and fastening apparatuses 104 of the lower portion or legs 113 of the compression shorts 100. The fastening apparatuses 104 are preferably Velcro® where the loops or cloth side of the Velcro® is attached to the fastening areas 102, and the hooks side of the Velcro® is on wraps 120 (FIGS. 5A-5D).

Figure 4:
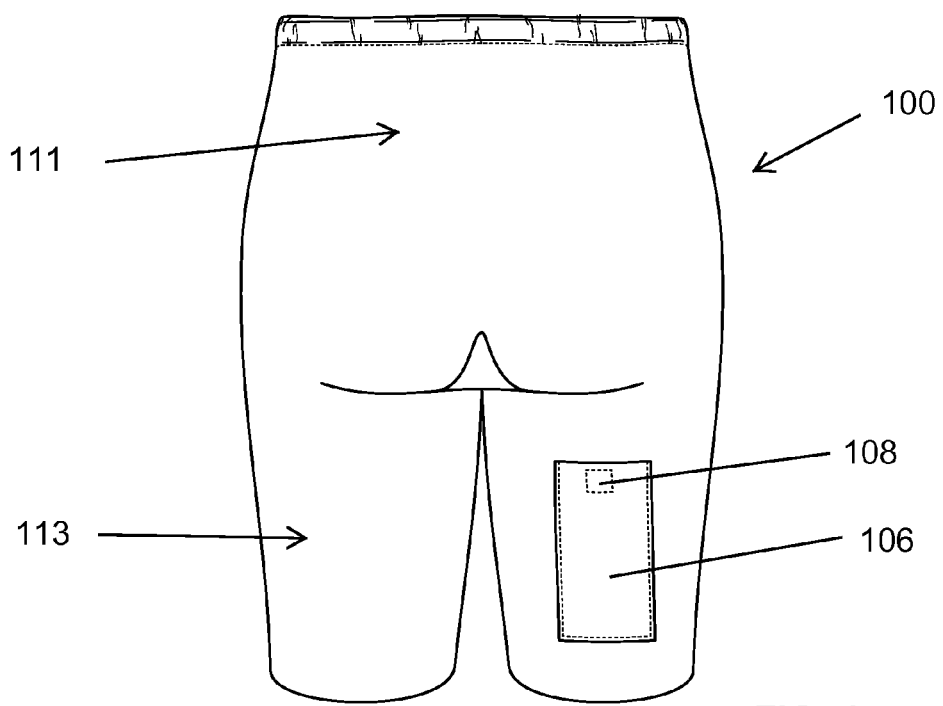
FIG. 4 is a rear view of the compression shorts shown in FIGS. 1-3.

FIG. 4 is a rear perspective view of the compression shorts 100 shown in FIGS. 1-3. The pocket 106 and closing apparatus 108 are shown on the lower portion 113 of the compression shorts 100.

Figures 5A, 5B:
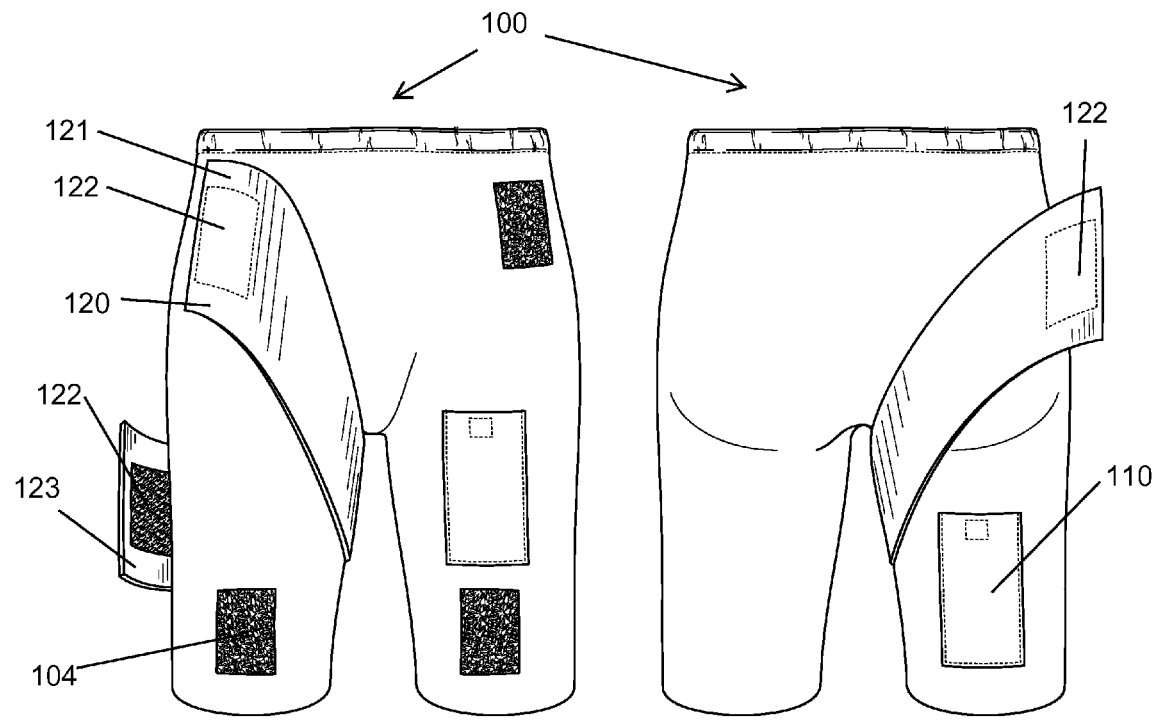
FIG. 5A is a front view of the compression shorts in FIGS. 1-4, wherein a compression wrap is starting to be wrapped around the right leg.
FIG. 5B is a rear view of the compression shorts shown in FIG. 5A including the compression wrap.
Figures 5C, 5D:
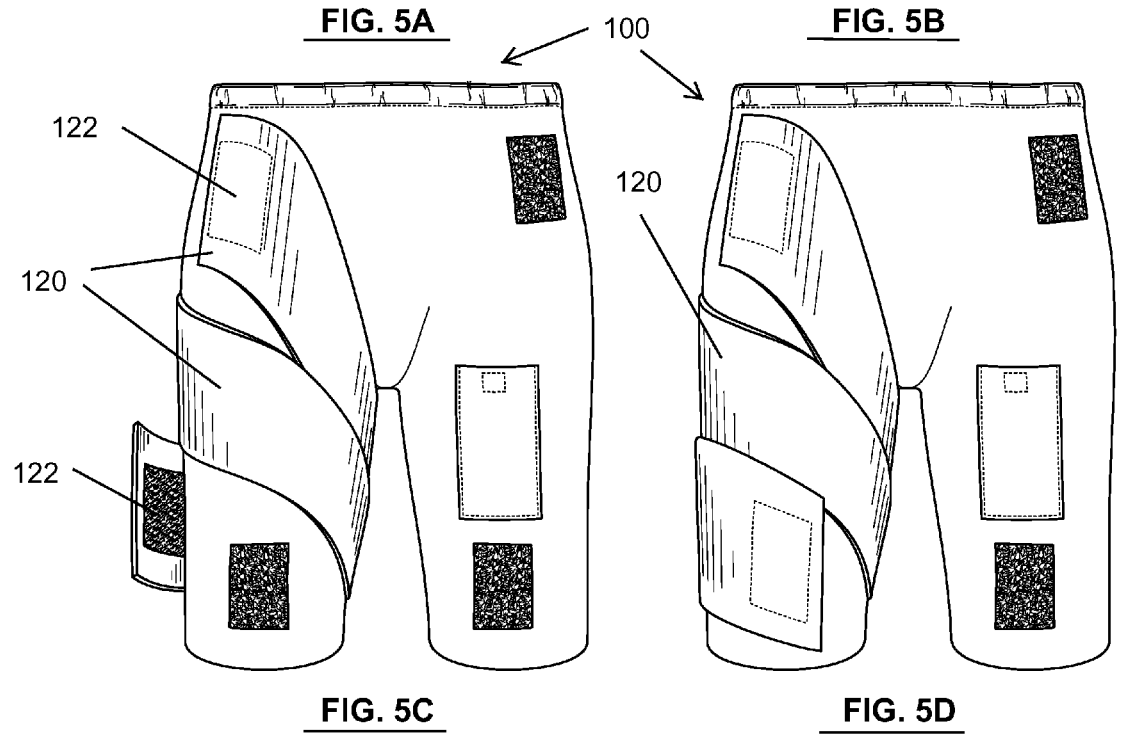
FIG. 5C is a front view of the compression shorts shown in FIGS. 5A and 5B, wherein the compression wrap is further wrapped around the right leg.
FIG. 5D is a front view of the compression shorts shown in FIGS. 5A-5C, wherein the compression wrapped is wrapped around and secured to the right leg.

FIGS. 5A-5D show multiple views of the compression shorts 100 shown in FIGS. 1-4, and a process of the applying a compression wrap 120 to the right leg 101 of the compression shorts, preferably while being worn by a user. FIG. 5A is a front view of the compression shorts 100, FIG. 5B is a rear view of the compression shorts 100, and FIGS. 5C and 5D are front views of the compression shorts 100. For illustration purposes, the wrap 120 is shown being applied to the right leg 101 and over the rear pocket 110. The wrap 120, of course, can be applied to the left leg 103 in a similar manner as the right leg 101, and a separate compression wrap 120 can be applied to each leg 101, 103 if necessary for physical treatment of multiple injuries.

Beginning with FIG. 5A, a first end 121 of the compression wrap 120 is secured to a fastening apparatus 104 on the front of the upper portion 111 of the compression shorts 100. A fastening apparatus 122 on the compression wrap 120, such as the hooks side of Velcro®, is secured to the loops side of the Velcro® on the fastening apparatus 104 on the front of the upper portion 111 of the compression shorts 100. The compression wrap 120 is then wrapped behind the right leg 101 of the compression shorts 100, as shown in FIG. 5B. The compression wrap 120 is preferably then wrapped around the rear of the right leg 101 again as shown in FIG. 5C, and in the process, covers at least a portion of rear pocket 106. In FIG. 5D the second end 123 of the compression wrap 120 is shown secured to the fastening apparatus 104 on the lower portion 113 on the front of the right leg 101, preferably by connecting the opposing loops and hooks of Velcro® 104, 122 on the compression shorts 100 and compression wrap 120, respectively. While the above description discusses wrapping the compression wrap 120 from the upper portion 111 around a leg to the lower portion 113 of the compression shorts 100, the compression wrap also can be applied by wrapping the compression wrap 120 from the lower portion 113 to the upper portion 111 of the compression shorts 100. Similarly, the compression wrap 120 can be applied to the compression shorts 100 to cover the front pocket 106.

As discussed above, the compression wrap 120 preferably is connected or secured to the compression shorts 100 via loop-and-hook fasteners at the hip or waist area of the compression shorts 100, and then can be wrapped around the groin and thigh area, creating compression for an injured or strained muscle and/or ligaments. Securing the compression wrap 120 with Velcro® at the hip or waist area will prevent the compression wrap 120 from sliding down the leg when a user is walking or otherwise moving about during regular daily activities or exercise.

While the preferred fastening areas 102 for the fastening apparatuses 104 are at the waist or hip area and just above the knee, there can be other fastening areas 102 with fastening apparatuses 104 along the compression shorts or leggings 100 to further restrict slippage of the compression wrap. 120. The form fitting compression shorts 100 and the compression wrap 120 further enable a user with an injury to wear a compression wrap under their clothing so that they can continue to treat their injury with compression while carrying on with their normal daily activities.

It should be noted that while the illustrated embodiment is compression shorts, the present invention also can just as easily be applied to leg wear and arm wear. For example, conventional socks or compression socks can be modified in accordance with the present invention to include fastening areas and fastening apparatuses as taught in the present invention. Similarly, conventional or compression arm wear can be modified in accordance with the present invention to include fastening areas and fastening apparatuses for compression wraps and pockets as taught in the present invention.

Although slipping of a flexible or compression wrap is more problematic with a quadriceps or hamstring injury, it also occurs with knee and calf injuries. The present invention can be applied to pants or full length leggings with loops-and-hooks or other fastening device at or near the knee and calf. The full length pants or leggings preferably are made of the same materials in order to help heal calf injures and shin splints. The full length pants or leggings can include pockets in front for shin splint injuries and in the back for calf injuries. With a full legging device configured in accordance with the present invention, a user with calf injuries or shin splints (common among runners) can be treated with compression, cold packs or heat packs, just as with a thigh, hamstring or groin injury as shown in the figures.

In other embodiments of the present invention the flexible or compression wrap 120 could be permanently attached to the compression shorts 100 with stitching at the waist or knee area, but one end would still need to remain unconnected with the hook and loop on one end in order to connect the wrap and prevent it from slipping during use. Although the drawings all show the use of Velcro® to secure the wrap 120 to the garment 100, it is possible that other means, such as snaps, zippers, buttons or the like could be used to secure wrap 120 and/or to secure the ice or heat pack 130 in the pocket 106, 110. It is also possible to have one end of the wrap 120 stitched to the garment 100 at the hip, with a fastening apparatus just at the knee. However, this may create problems with washing the physical treatment garment 100 if the compression wrap 120 is permanently attached to the garment 100. Thus, the preferred embodiment uses hooks-and-loops to fasten the flexible wrap 120 and to secure the ice and heat pack 130 within the pocket 110.

A physical treatment garment and compression wrap configured in accordance with the present invention can be used to treat a student athlete that has a leg injury or even allow them to participate in athletic events, even if the athlete has a minor strain. The physical treatment garment of the present invention can even be returned after the injury heals, so that a school has it available when another athlete has a leg injury.

In accordance with a further aspect of the present invention, the pockets 106 and 110 are added to the compression shorts 100 on the front and back of the thighs as shown in FIGS. 1-5D. The pockets 106, 110 can be sewn to either leg of the compression shorts or garment 100, and in front or in back or on the side of a leg of the compression shorts 100. The pockets 106, 110 can also be sewn onto the compression shorts 100 in multiple places on the same compression shorts 100, such as front, back, and sides of one or both legs of the compression shorts 100. Including pockets on all multiple locations on the compression shorts 100 is beneficial for athletic training facilities at high schools, colleges and universities that have athletic programs.

Figure 6:
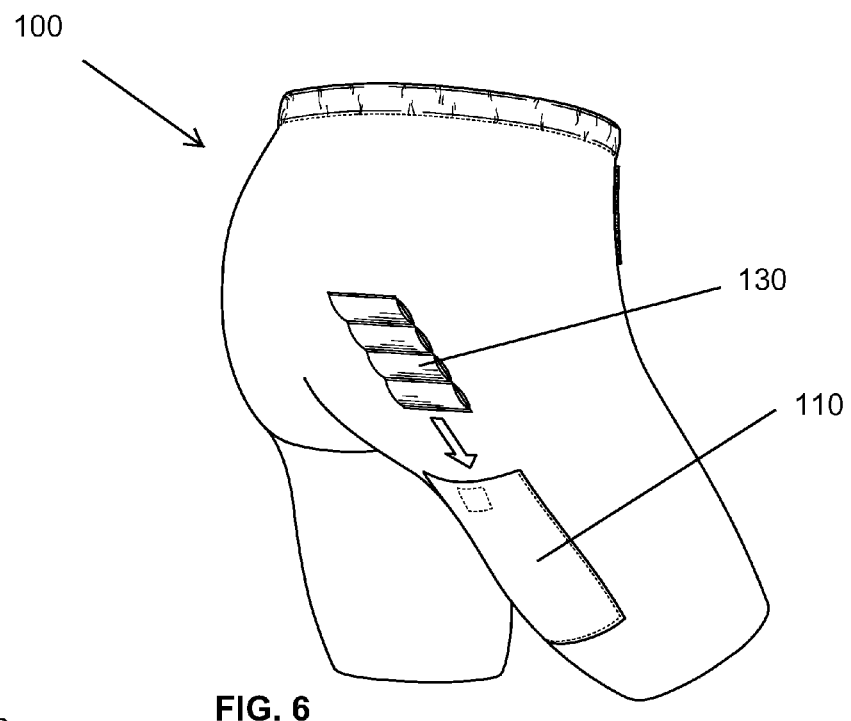
FIG. 6 is a rear perspective view of the compression shorts shown in FIGS. 1-4, wherein a pocket for holding a hot or cold pack in the rear of the right leg is illustrated.

FIG. 6 illustrates the pocket 110 on the rear of the right leg 101 of the compression shorts 100. Also illustrated is a heat or cold pack 130 being inserted into the rear pocket 110, and how an ice or heat pack can be inserted into the pocket 110 of the physical treatment garment 100 to treat the muscle injury, which in this example can be a hamstring.

In accordance with the present invention, the pockets 106, 110 can be used when needed to receive cold gel packs and/or heat packs 130 for treatment of an injury. The pockets 106, 110 preferably are constructed of the same or similar flexible fabric as the compression shorts 100. The fastening apparatuses 108, 112 on the pockets 106, 110, respectively, can be opened or closed with loops-and-hooks or another fastening device, such as a zipper, snaps or buttons. The pockets 106, 110 allow a user to insert a cold pack (such as a cold gel pack) or heat pack (such as a hot water bottle or disposable heat packs commonly known as hand warmers) 130 and still be able to move about while treating their injury with cold or heat.

Figure 7:
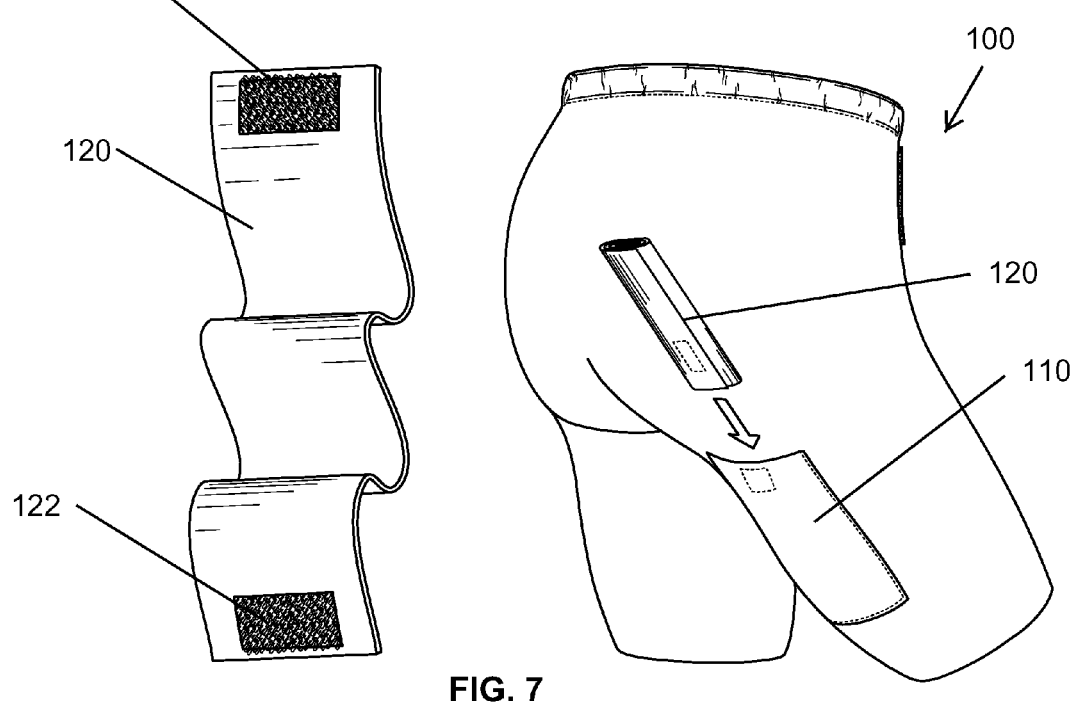
FIG. 7 is a rear perspective view of the compression shorts shown in FIGS. 1-4, wherein a pocket for holding a folded compression wrap in the rear of right leg is illustrated, and both an unfolded and folded compression wrap are illustrated.

FIG. 7 shows how a compressing wrap 120 can be folded or rolled up and stored in the pocket 110 when the compression shorts 100 are not being used to treat muscle injuries.

Figure 8:
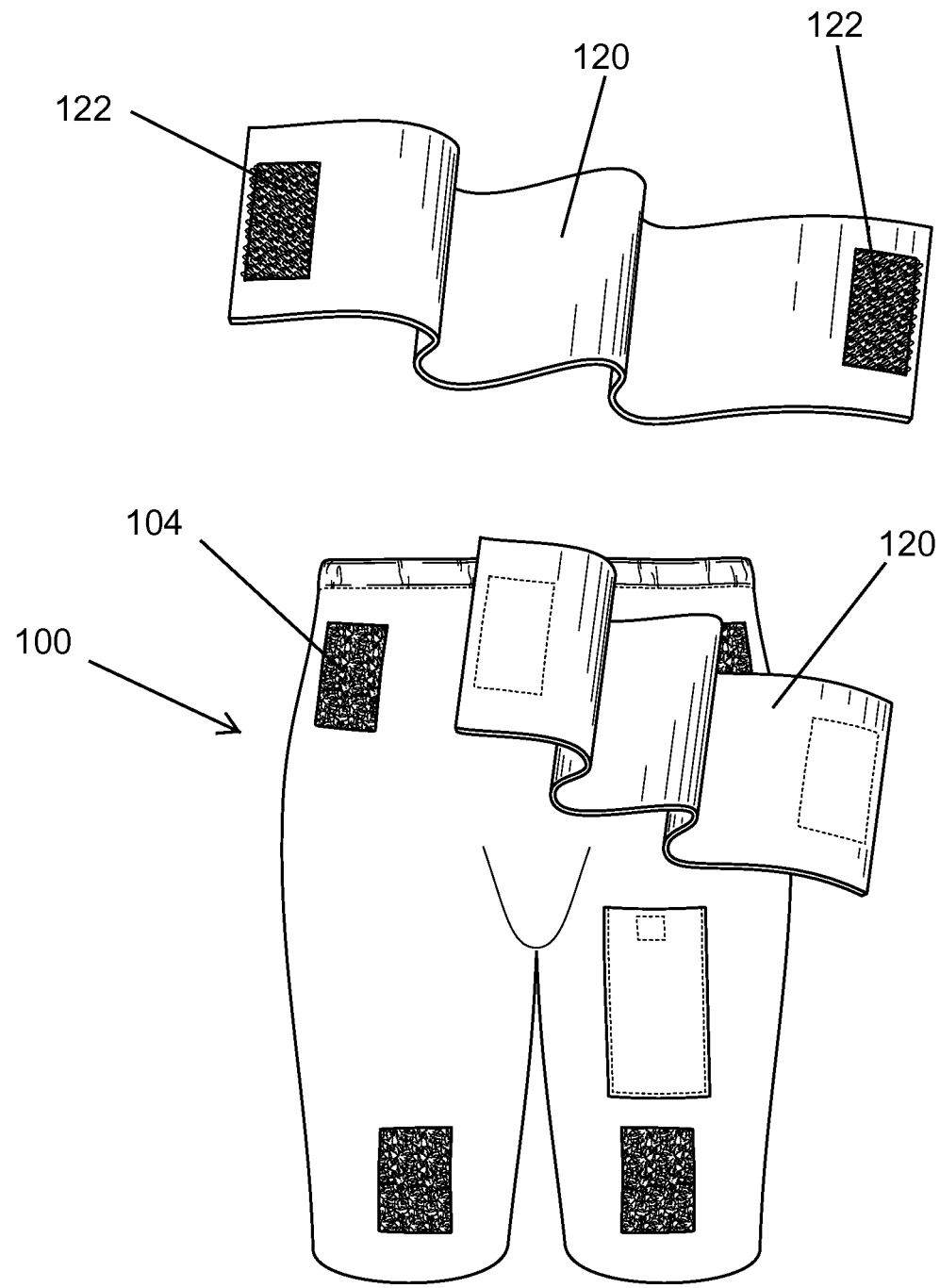
FIG. 8 is a front view of the compression shorts shown in FIGS. 1-4, wherein a compression wrap is shown being connected to the front of the compression shorts.

FIG. 8 is another view from the front of the compression shorts 100, wherein the compression wrap 120 is secured to the fastening apparatus 104 on the upper portion 111 of the compression shorts 100. As illustrated in FIG. 8, the locations and arrangement of the compression wrap 120 is secured to the compression shorts 100 and can be varied to treat different injuries.

FIG. 9 is a side view of the compression wrap 120 being wrapped around the right leg 101 of the compression shorts 100 as previously shown in FIG. 5D. The connection at the hip/waist area 111 and at the knee or just above the knee area 113 demonstrate how the compression shorts or physical treatment garment 100 will keep the wrap 120 in place when a wearer of the compression shorts 100 is working and/or performing normal every day activities while maintaining compression treatment.

FIG. 10 is a rear perspective view of the rear pocket 110 of the compression shorts 100 and demonstrates how a gel pack 130 can be inserted into the pocket 110 and secured within the pocket 110 using the fastening apparatus 112 with hooks-and-loops, or other fastening device.

FIG. 10a is an enlarged view of the fastening apparatus 112 on the pocket 110. As shown in FIG. 10a, the fastening apparatus 112 is Velcro®, wherein the cloth or loops portion 114 of the Velcro® preferably is on the compression shorts 100, and the hooks portion 115 of the Velcro® preferably is on the inside back of the pocket 110.

FIG. 11 is a side perspective view of a full length physical therapy garment (pants/tights/leggings) 138 showing the fastening hook-and-loop (Velcro®) at the knee area 140 and ankle area 142 for securing the flexible compression wrap around the lower calf and shin area and a pocket for securing an ice pack or heat pack 144 for treatment of a calf or shin splint injury.

FIG. 12 is a front perspective view of the full length physical therapy garment (pants/tights/leggings) 138 showing the fastening hook-and-loop (Velcro®) at the knee area 140 and ankle area 142 for securing the flexible compression wrap around the lower calf and shin area and a pocket for securing an ice pack or heat pack 144 for treatment of a calf or shin splint injury.

FIG. 13 is a rear perspective view of the full length physical therapy garment (pants/tights/leggings) 138 showing the fastening hook-and-loop (Velcro®) at the knee area 140 and ankle area 142 for securing the flexible compression wrap around the lower calf and shin area and a pocket for securing an ice pack or heat pack 144 for treatment of a calf or shin splint injury.

FIG. 14 is a front perspective view of a physical therapy garment (compression shirt) 148 showing the fastening hook-and-loop (Velcro®) at the shoulder area 150 and elbow area 152 for securing a flexible compression wrap around the arm and a pocket for securing an ice pack or heat pack 154 for treatment of a bicep or triceps injury.

While specific embodiments have been shown and described to point out fundamental and novel features of the invention as applied to the preferred embodiments, it will be understood that various omissions and substitutions and changes of the form and details of the invention illustrated and in the operation may be done by those skilled in the art, without departing from the spirit of the invention.

The invention claimed is:

1. A physical treatment garment, comprising:
   a pair of flexible shorts constructed of flexible material;
   a plurality of fastening apparatuses on multiple fastening areas on the pair of flexible shorts;
   a flexible wrap having a first end with a fastening apparatus and a second end with a fastening apparatus for releasably coupling the flexible wrap to the fastening apparatuses on the pair of flexible shorts, wherein the first end and the second end of the flexible wrap each can be attached to a fastening apparatus on the pair of flexible shorts to apply compression to an injured area, and the flexible wrap can be completely removed from the pair of flexible shorts for cleaning; and
   wherein at least one of the plurality of the fastening apparatuses on the pair of flexible shorts is located on an upper portion proximate to a hip and waist area of the pair of flexible shorts, and at least a second of the plurality of the fastening apparatuses on pair of the shorts is located on a lower portion of the flexible shorts proximate just above a knee area, thereby enabling the flexible wrap can be connected to the pair of flexible shorts by the plurality of fastening apparatuses between the upper portion and the lower portion of the pair of flexible shorts to provide compression treatment to thigh, groin and hamstring areas of a user's body.

2. The physical treatment garment of claim 1, wherein the fastening apparatuses on the pair of the flexible shorts include hooks-and-loops, and the fastening apparatuses on the flexible wrap include reciprocal hooks-and-loops to secure the flexible wrap to the pair of flexible shorts.

3. The physical treatment garment of claim 1, wherein the fastening apparatuses on the pair of flexible shorts include buttons and the fastening apparatuses on the flexible wrap includes button holes.

4. The physical treatment garment of claim 1, wherein the fastening apparatuses on the pair of flexible shorts and the flexible wrap include zippers to secure the flexible wrap to the pair of flexible shorts.

5. The physical treatment garment of claim 1, wherein the fastening apparatuses on the pair of flexible shorts and the flexible wrap include snaps for securing the flexible wrap to the pair of flexible shorts.

6. The physical treatment garment of claim 1, wherein the pair of flexible shorts include a pocket on a front and lower portion of the pair of flexible shorts, and wherein the pocket includes a fastening apparatus for closing the pocket so as to secure a gel pack within the pocket for treating an injury.

7. The physical treatment garment of claim 1, wherein the pair of flexible shorts include a pocket on a rear and lower portion of the pair of flexible shorts, and the pocket includes a fastening apparatus for closing the pocket so as to secure a gel pack within the pocket for treating an injury.

8. The physical treatment garment of claim 1, further comprising:
   a second flexible wrap having a third end with a fastening apparatus and a fourth end with a fastening apparatus for releasably coupling the second flexible wrap to the fastening apparatuses on the pair of flexible shorts, wherein the third end and the fourth end of the flexible wrap each can be attached to a fastening apparatus on the pair of flexible shorts to apply compression to an injured area, and the flexible wrap can be completely removed from the pair of flexible shorts for cleaning.

9. The physical treatment garment of claim 1, wherein the flexible wrap is to be wrapped around a leg of a user.

10. A physical treatment garment, comprising:
    a pair of flexible shorts constructed of flexible material;
    a plurality of fastening apparatuses on multiple fastening areas on the pair of shorts; and
    a flexible wrap having a first end and a second end, wherein the first end of the flexible wrap is permanently connected to an upper portion proximate to a hip and waist area of the pair of flexible shorts, and the second end of the flexible wrap includes a fastening apparatus to be releasably secured to one of the plurality of fastening apparatuses on a lower portion of the flexible shorts proximate just above a knee area to apply compression to an injured area.

11. The physical treatment garment of claim 10, wherein the plurality of fastening apparatuses on the pair of flexible shorts include hooks-and-loops, and the fastening apparatus on the second end of flexible wrap includes reciprocal hooks-and-loops to secure the flexible wrap to the physical treatment garment.

12. The physical treatment garment of claim 10, wherein the fastening apparatus on the second end of the flexible wrap includes a snap for securing the flexible wrap to the pair of flexible shorts.

13. The physical treatment garment of claim 10, wherein the pair of flexible shorts include a pocket on a front and lower portion of the pair of flexible shorts, and wherein the pocket includes a fastening apparatus for closing the pocket so as to secure a gel pack within the pocket for treating an injury.

14. The physical treatment garment of claim 10, wherein the flexible pair of flexible shorts include a pocket on a rear and lower portion of the pair of flexible shorts, and the pocket includes a fastening apparatus for closing the pocket so as to secure a gel pack within the pocket for treating an injury.

15. A physical treatment garment, comprising:
    a pair of shorts constructed of flexible material;
    a plurality of fastening apparatus on the pair of shorts, and at least one of the fastening apparatuses is located on an upper portion proximate to a hip and waist area of the pair of shorts, and at least one of the fastening apparatus is located on a lower portion of the pair of shorts proximate just above a knee area;
    a flexible wrap having a first end and a second end; and
    a plurality of fastening apparatuses on the flexible wrap, wherein at least one of the plurality of fastening apparatuses on the flexible wrap is on the first end and at least one of the plurality of fastening apparatuses on the flexible wrap is on the second end for releasably coupling the flexible wrap to the fastening apparatuses on the pair of shorts, and wherein the first end and the second end of the flexible wrap each can be attached to a fastening apparatus on the pair of shorts to apply compression to an injured area, and the flexible wrap can be completely removed from the pair of shorts for cleaning.

16. The physical treatment garment of claim 15, wherein the plurality of fastening apparatuses on the pair of flexible shorts includes hooks-and-loops, and the plurality of fastening apparatuses on the flexible wrap includes reciprocal hooks-and-loops to secure the flexible wrap to the pair of flexible shorts.

17. The physical treatment garment of claim 15, wherein the pair of flexible shorts include a pocket on a front and lower portion of the pair of flexible shorts, and wherein the pocket includes a fastening apparatus for closing the pocket so as to secure a gel pack within the pocket for treating an injury.

18. The physical treatment garment of claim 15, wherein the pair of flexible shorts includes a pocket on a rear and lower portion of the pair of flexible shorts, and the pocket includes a fastening apparatus for closing the pocket so as to secure a gel pack within the pocket for treating an injury.

* * * * *